(12) United States Patent
Holmqvist

(10) Patent No.: US 9,662,448 B2
(45) Date of Patent: May 30, 2017

(54) MEDICAMENT DELIVERY DEVICE

(71) Applicant: Carebay Europe Ltd, Swatar (MT)

(72) Inventor: Anders Holmqvist, Värmdö (SE)

(73) Assignee: Carebay Europe Ltd, Sliema (MT)

(*) Notice: Subject to any disclaimer, the term of this patent is extended or adjusted under 35 U.S.C. 154(b) by 72 days.

(21) Appl. No.: 14/385,162

(22) PCT Filed: Mar. 7, 2013

(86) PCT No.: PCT/EP2013/054580
§ 371 (c)(1),
(2) Date: Sep. 14, 2014

(87) PCT Pub. No.: WO2013/135551
PCT Pub. Date: Sep. 19, 2013

(65) Prior Publication Data
US 2015/0051550 A1    Feb. 19, 2015

Related U.S. Application Data

(60) Provisional application No. 61/611,654, filed on Mar. 16, 2012.

(30) Foreign Application Priority Data

Mar. 16, 2012  (SE) ........................ 1250250

(51) Int. Cl.
*A61M 5/20* (2006.01)
*A61M 5/31* (2006.01)
*A61M 5/315* (2006.01)

(52) U.S. Cl.
CPC ............. *A61M 5/20* (2013.01); *A61M 5/2033* (2013.01); *A61M 5/3129* (2013.01);
(Continued)

(58) Field of Classification Search
CPC .................. A61M 5/20; A61M 5/2033; A61M 2005/2026; A61M 2205/8281; A61M 2005/202
See application file for complete search history.

(56) References Cited

U.S. PATENT DOCUMENTS

| | | | |
|---|---|---|---|
| 6,942,650 B1 * | 9/2005 | Schultz .................. | B01D 46/24 454/66 |
| 2006/0276753 A1 * | 12/2006 | Kronestedt ............. | A61M 5/20 604/186 |
| 2014/0088515 A1 | 3/2014 | Karlsson | |

FOREIGN PATENT DOCUMENTS

| | | |
|---|---|---|
| EP | 1728529 A1 | 12/2006 |
| WO | 2006/130100 A1 | 12/2006 |

(Continued)

OTHER PUBLICATIONS

EPO, Int'l Search Report in PCT/EP2013/054580, Jul. 26, 2013, pp. 1-3.
(Continued)

*Primary Examiner* — Bradley Osinski
(74) *Attorney, Agent, or Firm* — Piedmont Intellectual Property

(57) ABSTRACT

The present invention relates to a medicament delivery device comprising a housing (10), which housing (10) is arranged ranged to accommodate a medicament container (16), the device further comprises a drive mechanism (18) capable of, upon activation, expel a dose of medicament from said medicament container, the drive mechanism comprising a flat spiral spring (26). The invention is characterized in that at least a part (36) of an outermost turn of said flat spiral spring (26) is positioned on an outer surface of said housing (10).

16 Claims, 4 Drawing Sheets

(52) U.S. Cl.
CPC ... *A61M 5/31583* (2013.01); *A61M 2005/202* (2013.01); *A61M 2005/2026* (2013.01); *A61M 2205/59* (2013.01); *A61M 2205/60* (2013.01); *A61M 2205/8281* (2013.01)

(56) References Cited

FOREIGN PATENT DOCUMENTS

| | | |
|---|---|---|
| WO | 2009/037141 A1 | 3/2009 |
| WO | 2011/025448 A1 | 3/2011 |

OTHER PUBLICATIONS

EPO, Written Opinion in PCT/EP2013/054580, Jul. 26, 2013, pp. 1-6.

\* cited by examiner

MEDICAMENT DELIVERY DEVICE

TECHNICAL AREA

The present invention relates to a medicament delivery device and in particular a medicament delivery device arranged with a delivery drive mechanism comprising a flat spiral spring.

BACKGROUND OF INVENTION

Many different medicament delivery devices have been developed and designed which have been provided with automatic functions such as automatic dose delivery when activated. The automatic functions are in many cases performed by energy members such as springs that are in a tensioned state before activation.

For many medicament delivery devices, compression springs have been used to a large extent. Some of the advantages with compression springs are the reliable performance and the low manufacturing cost. Some of the disadvantages are that the devices tend to be long and that force delivered is reduced when the spring is extended, leading to possible problems to deliver enough force through the whole stroke. Therefore, in order to ascertain enough force, the springs are often designed such that the initial force is very high, usually unnecessarily high. This provides additional problems especially when the spring is pre-tensioned during assembly of the medicament delivery device because the high built-in forces from the spring may cause material deformation, which in turn may cause breakage or mal-function of the medicament delivery device.

Some developers have then turned to other types of energy members because of the drawbacks with compression springs. One type of energy members that have been considered is a type of flat spiral spring, in the form of a steel band wound to a package. The inner end is then often attached to a drive member of the medicament delivery device while the outer end is attached to a component that can be fixed in relation to the housing. In order to pre-tension the spring, the package is tightened by turning the outer end of the spring in relation to the inner end of the spring, or vice versa.

This type of spring provides much less built-in force when pre-tensioned and also the built-in forces have a better force distribution in the device than the compression springs. One of the devices that utilize the above mentioned type of spring is disclosed in document WO 2009/037141. However, one aspect that may be regarded as a drawback with this type of spring is that the diameter of the device tends to be larger than a more conventional pen-type medicament delivery device. This is mainly due to the spring package and also that the outer end of the spring has to be attached to a housing component that obviously has to be outside the spring as seen in a radial direction, thereby adding to the thickness of the medicament delivery device.

BRIEF DESCRIPTION OF INVENTION

In the present application, when the term "distal" is used, this refers to the direction pointing away from the dose delivery site. When the term "distal part/end" is used, this refers to the part/end of the delivery device, or the parts/ends of the members thereof, which is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site.

The aim with the present invention is to reduce the drawbacks regarding size when using an energy accumulating member or a force member in the form of a flat spiral spring.

This aim is obtained by a medicament delivery device according to the features of the independent patent claims. Preferable embodiments of the invention form the subject of the dependent patent claims.

The medicament delivery device according to the present invention may comprise a housing, which housing is arranged to accommodate a medicament container. It is to be understood that the housing may comprise one or several housing parts, fixedly or releasibly attached to each other. The medicament container may have a number of different designs such as syringes, cartridges, etc.

Preferably, the device may further comprise a drive mechanism capable of, upon activation, expel a dose of medicament from said medicament container. The drive mechanism is capable of acting on the medicament container such as for example a plunger rod arranged to push on a stopper placed inside the medicament container.

According to the present invention, the drive mechanism comprises a flat spiral spring. The flat spiral spring may be wound a number of turns depending on the force required from the spring to be capable of expelling a dose of medicament.

According to a preferable solution according to the present invention, at least a part of an outermost turn of said flat spiral spring is positioned on an outer surface of said housing. This means that a length of the flat spiral spring is outside, as seen in a generally radial direction, of the housing.

By this design, not the entire length of the flat spiral spring is inside the housing, whereby the overall diameter of the medicament delivery device is reduced. According to a favourable design, the outermost turn of said spring runs along the circumference of said housing, whereby the full circumference on the outer surface of the housing is utilized.

In this aspect, the outermost turn may be covered by for example a sticker or another thin layer of material that does not add to the diameter of the device in any substantial way.

On the other hand, if the steel strip of the spring is visible, it may add to the overall appearance of the device in a positive way, providing a characteristic distinguishing feature of quality and uniqueness.

In order not to increase the diameter of the device, the attachment means of the outer end of said spring generally should coincide with the outer surface of said housing. In this way, save of goods in manufacturing a high number of housings is achieved.

Depending on the intended appearance, the housing may be arranged with a groove or seat in which the strip of the spring may be positioned. Further the housing may be arranged with at least one opening through which the spring extends.

When an opening is arranged, then an attachment means could constitute one edge of said opening, around which edge the outer end of said spring is formed. In this manner, no extra feature or design has to be arranged, the present opening feature could be utilized.

On the other hand, or in addition the attachment means could comprise at least one rivet, at least one screw, at least one nut and bolt or glue.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
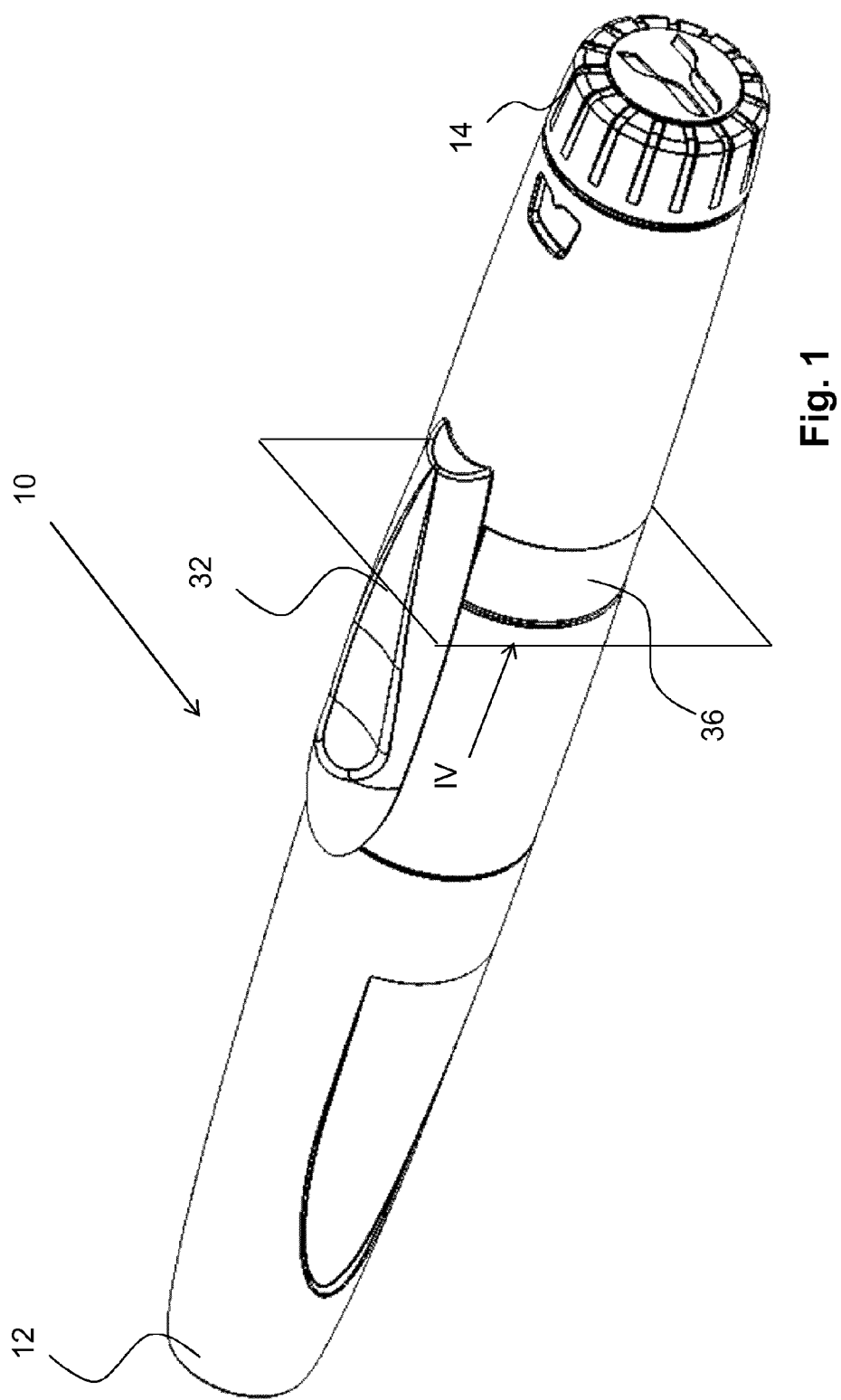
FIG. 1 shows a perspective view of a medicament delivery device according to the present invention.
Figure 2:
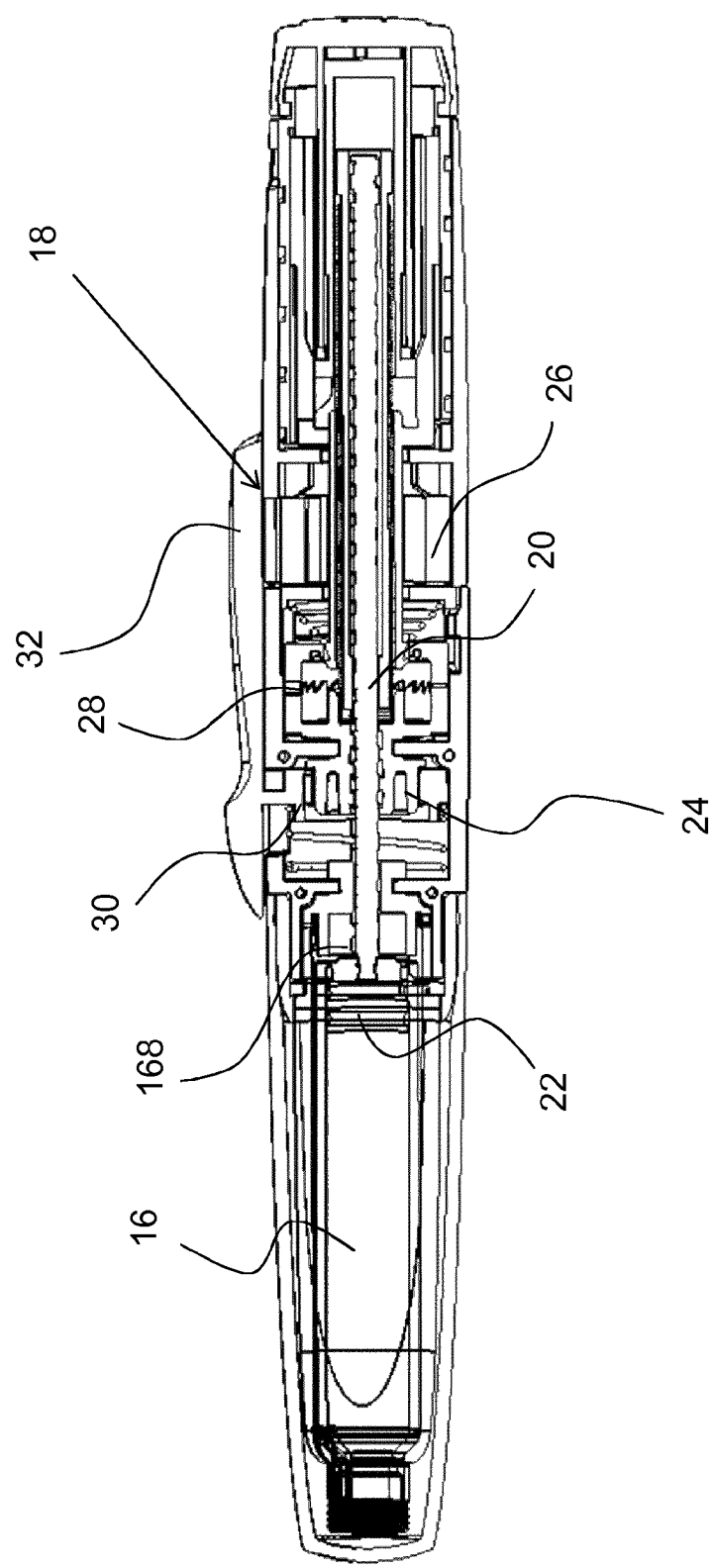
FIG. 2 is a cross-sectional longitudinal view of the device of FIG. 1

The device shown in the drawings comprises a generally elongated housing 10 extending along an axial axis A and having a proximal end 12 and a distal end 14, FIG. 1. It is to be understood that the housing may comprise one or several housing parts, fixedly or releasibly attached to each other. Thus, the elongated housing 10 may comprise a proximal housing and a distal housing. A medicament container 16, FIG. 2, may be positioned inside a proximal part of the housing 10 or inside the proximal housing.

The medicament delivery device is further arranged with a drive mechanism 18 for expelling medicament from the medicament container 16 upon activation. The medicament delivery device is of the general type disclosed in WO 2006130100A1, in WO2011025448A1, and in the Swedish patent application SE1150427-1. To the extent not inconsistent with this disclosure, the disclosures of WO 2006130100A1, WO2011025448A1 and of the Swedish patent application SE1150427-1 are incorporated herein by reference.

Figure 3:
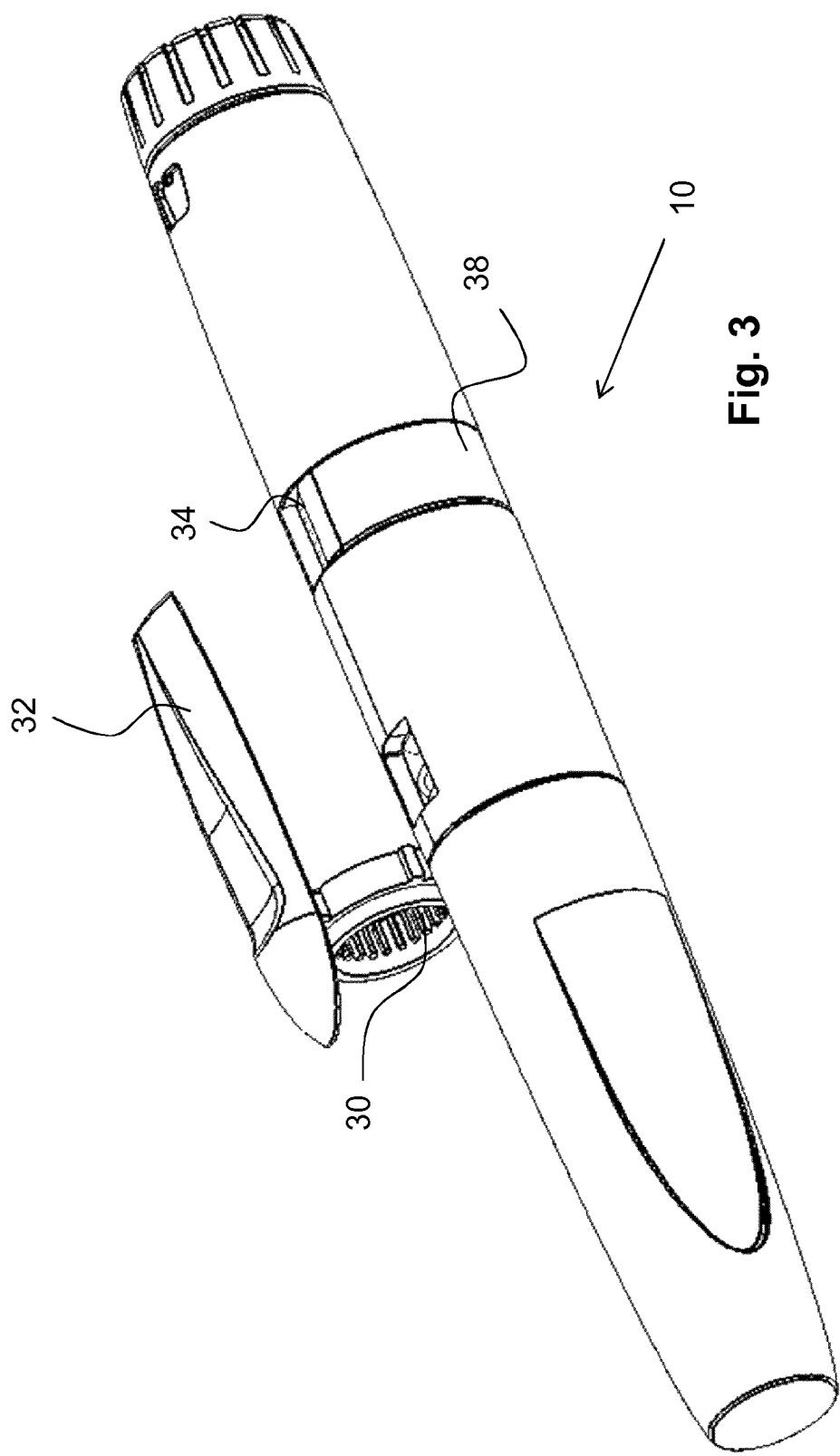
FIG. 3 shows the device of FIG. 1 with an actuation member removed.

In the present embodiment, the drive mechanism 18 is located within a distal part of the housing 10 or inside the distal housing and comprises a plunger rod or a driving plunger 20, a drive nut 24, a flat spiral spring 26 and a drive member 28 among other components. In the embodiment shown the plunger rod is an elongated threaded plunger rod 20, FIG. 2, capable of acting on a stopper 22 inside the medicament container 16. The plunger rod 20 is arranged to cooperate with the drive nut 24, which drive nut 24 is threaded onto the plunger rod 20. The drive nut 24 is drivably connected to the flat spiral spring 26 via the drive member 28. Said flat spiral spring is a clock spring, a variable force spring, a constant force spring, a power spring, a torque spring, a negator or the like having a predetermined number of turns, wherein the outermost turn has an outer end connected to the housing. The drive nut 24 is further connected to an actuation member 30, FIGS. 2 and 3, which actuation member comprises an activation button 32, wherein the activation button 32 and the actuation member are arranged to be moved manually from a position where the actuation member 30 locks rotation of the drive nut 24 to a position where the drive nut 24 is free to rotate.

According to the present invention, the flat spiral spring 26 is arranged as follows. The housing 10 is arranged with an opening 34, preferably a longitudinally extending opening. At least part of the outermost turn 36 of the spring 26 is positioned on the outer surface of the housing 10, and preferably on a circumferential groove or seat 38 on the outer surface of the housing, FIG. 3, such that said at least part of the outermost turn 36 of the spring 26 is visible. The outer end of the spring 26 is then attached to the housing 10 and in the embodiment shown the attachment is performed by an inwardly bend 40, FIG. 4, of the outer end of the spring 26, which bend 40 surrounds an edge 42 of the opening 34.

Figure 4:
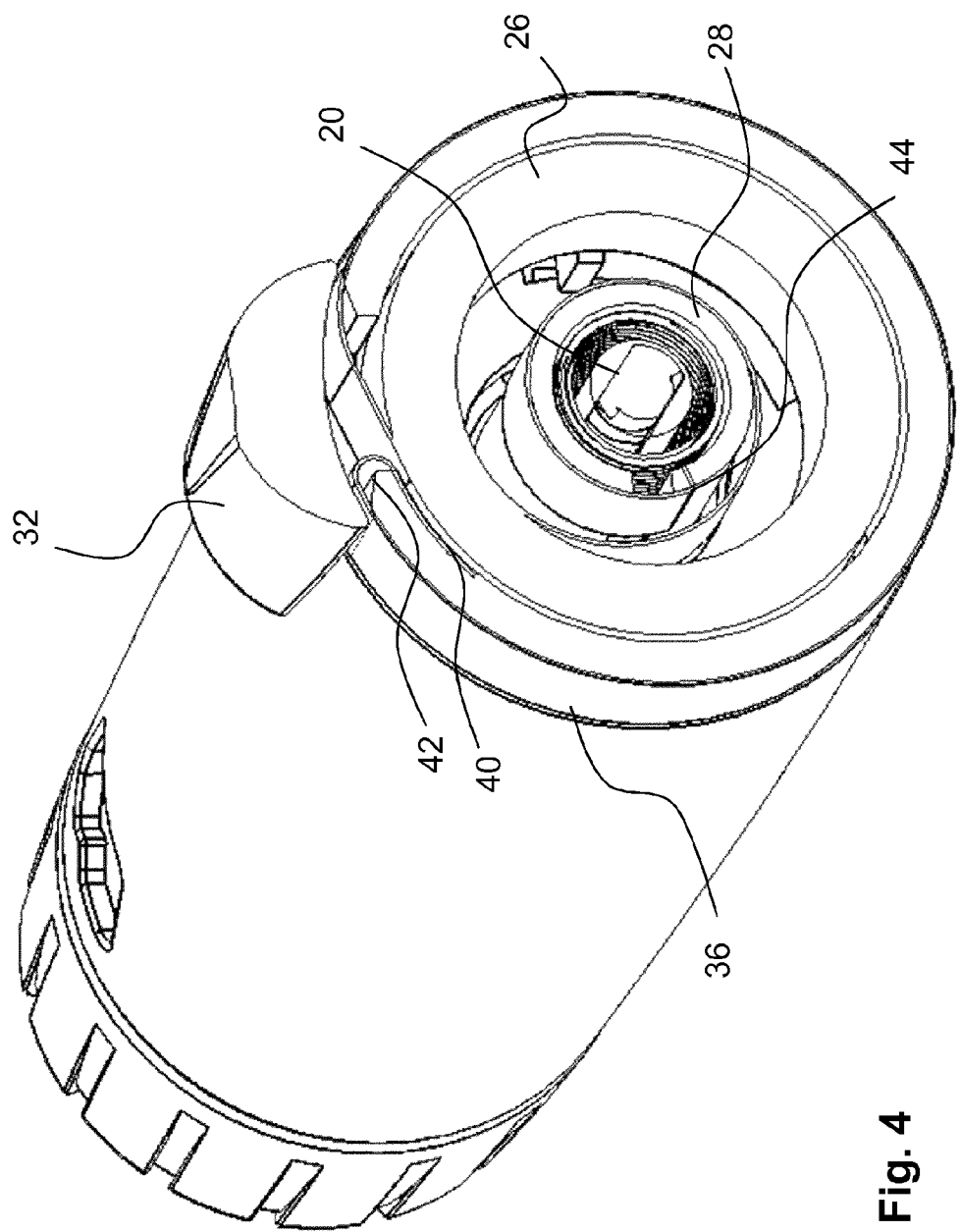
FIG. 4 shows a cross-section taken along the plane IV-IV of FIG. 1.

The rest of the spring package i.e. the inner turns is positioned inside the housing with possible guides on each side of the spring package. The inner end 44, FIG. 4, of the flat spiral spring 26 is then attached to the drive member 28, which in turn is operably attached to the drive nut 24. The activation button 32 may be positioned such that the opening is covered by the button 32, as seen in FIG. 4, thereby reducing the risk of foreign matter as e.g. dust entering into the device.

It is to be understood that the embodiment described above and shown in the drawings is to be regarded only as a non-limiting example of the invention and that it may be modified in many ways within the scope of the patent claims.

The invention claimed is:

1. A medicament delivery device, comprising:
an elongated outer housing configured for accommodating a medicament container; and
a drive mechanism configured for expelling a dose of medicament from the medicament container upon activation, wherein the drive mechanism includes a flat spiral spring having a predetermined number of turns, an outermost turn has an outer end connected directly to the elongated outer housing, at least a majority of the outermost turn is positioned on an outer surface of the elongated outer housing, and the outermost turn runs along a circumference of the outer surface of the elongated outer housing.

2. The medicament delivery device of claim 1, wherein the outer end includes an attachment device that coincides with the outer surface.

3. The medicament delivery device of claim 2, wherein the attachment device comprises at least one rivet.

4. The medicament delivery device of claim 2, wherein the attachment device comprises at least one screw.

5. The medicament delivery device of claim 2, wherein the attachment device comprises at least one nut and at least one bolt.

6. The medicament delivery device of claim 2, wherein the attachment device comprises glue.

7. The medicament delivery device of claim 1, wherein the outer surface of the elongated outer housing includes a circumferential groove or seat configured for accommodating the outermost turn.

8. The medicament delivery device of claim 1, wherein the part of the outermost turn is visible.

9. The medicament delivery device of claim 1, wherein the elongated outer housing includes an opening, through which the flat spiral spring runs.

10. The medicament delivery device of claim 9, wherein the outer end includes an attachment device that coincides with the outer surface.

11. The medicament delivery device of claim 10, wherein the attachment device comprises an edge of the opening, and the outer end is formed around the edge.

12. The medicament delivery device of claim 10, wherein the attachment device comprises at least one rivet.

13. The medicament delivery device of claim 10, wherein the attachment device comprises at least one screw.

14. The medicament delivery device of claim 10, wherein the attachment device comprises at least one nut and at least one bolt.

15. The medicament delivery device of claim 10, wherein the attachment device comprises glue.

16. The medicament delivery device of claim 10, wherein the part of the outermost turn is visible.

\* \* \* \* \*